(12) United States Patent
Detrick et al.

(10) Patent No.: US 10,384,988 B2
(45) Date of Patent: Aug. 20, 2019

(54) CHLORIDE MANAGEMENT IN IONIC LIQUID ALKYLATION PROCESSES

(71) Applicant: UOP LLC, Des Plaines, IL (US)

(72) Inventors: Kurt Detrick, Glen Ellyn, IL (US); Douglas A. Nafis, Mount Prospect, IL (US); David A. Wegerer, Lisle, IL (US); Eric Leeton, Corpus Christi, TX (US); Trung Pham, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 57 days.

(21) Appl. No.: 15/346,561

(22) Filed: Nov. 8, 2016

(65) Prior Publication Data
US 2017/0183275 A1  Jun. 29, 2017

Related U.S. Application Data

(60) Provisional application No. 62/387,127, filed on Dec. 23, 2015.

(51) Int. Cl.
*C07C 2/60* (2006.01)
*C07C 7/09* (2006.01)
*C07C 9/12* (2006.01)
*C07C 7/148* (2006.01)

(52) U.S. Cl.
CPC .................. *C07C 2/60* (2013.01); *C07C 7/09* (2013.01); *C07C 7/148* (2013.01)

(58) Field of Classification Search
CPC .............. C07C 2/60; C07C 7/09; C07C 7/148
See application file for complete search history.

(56) References Cited

U.S. PATENT DOCUMENTS

| 2,408,950 A | 10/1946 | Pines et al. |
| 2,583,352 A | 1/1952 | Berg |
| 4,307,254 A | 12/1981 | Smith, Jr. |
| 4,764,440 A | 8/1988 | Jones et al. |
| 5,104,840 A | 4/1992 | Chauvin et al. |
| 5,824,832 A | 10/1998 | Sherif et al. |
| 7,538,256 B2 | 5/2009 | Driver et al. |

(Continued)

FOREIGN PATENT DOCUMENTS

| EP | 523164 B1 | 11/1995 |
| EP | 1354863 B1 | 6/2005 |

OTHER PUBLICATIONS

Lieberman., "Troubleshooting process operations—12. (A discussion of) processes (which) show signs of fouled trays", Oil Gas Journal (1981), v 79, n 5, p. 98,100-101.

(Continued)

*Primary Examiner* — In Suk C Bullock
*Assistant Examiner* — Ali Z Fadhel

(57) ABSTRACT

The present invention involves processes and equipment for handling chloride in an ionic liquid alkylation system. The processes involve not only breaking down the organic chloride to active HCl for ionic liquid activation, but also recovering HCl in the effluent downstream to maintain the HCl requirements while also reducing HCl emissions. This equipment may be used in conjunction with an isomerization reaction zone which is integrated into the ionic liquid alkylation process to further isomerize n-paraffins to isoparaffins for recycle to the alkylation reaction zone.

20 Claims, 7 Drawing Sheets

(56) References Cited

U.S. PATENT DOCUMENTS

| | | |
|---|---|---|
| 7,651,970 B2 | 1/2010 | Elomari et al. |
| 7,674,739 B2 | 3/2010 | Elomari et al. |
| 7,674,740 B2 | 3/2010 | Harris et al. |
| 7,678,727 B2 | 3/2010 | Harris et al. |
| 7,691,771 B2 | 4/2010 | Harris et al. |
| 7,727,925 B2 | 6/2010 | Elomari et al. |
| 7,732,363 B2 | 6/2010 | Elomari et al. |
| 7,737,067 B2 | 6/2010 | Elomari et al. |
| 7,825,055 B2 | 11/2010 | Elomari et al. |
| 7,902,415 B2 | 3/2011 | Small |
| 7,955,498 B2 | 6/2011 | Driver et al. |
| 7,956,002 B2 | 6/2011 | Elomari et al. |
| 7,956,230 B2 | 6/2011 | Timken et al. |
| 8,524,623 B2 | 9/2013 | Timken et al. |
| 8,709,236 B2 | 4/2014 | Serban et al. |
| 8,795,515 B2 | 8/2014 | Zhan et al. |
| 9,079,175 B1 | 7/2015 | Smith et al. |
| 9,079,176 B1 | 7/2015 | Smith et al. |
| 9,233,928 B2 | 1/2016 | Broderick et al. |
| 2007/0249485 A1 | 10/2007 | Elomari et al. |
| 2009/0163750 A1 | 6/2009 | Timken et al. |
| 2009/0163755 A1 | 6/2009 | Small |
| 2009/0192339 A1 | 7/2009 | Timken et al. |
| 2011/0092753 A1 | 4/2011 | Zhan et al. |
| 2011/0144399 A1 | 6/2011 | Elomari et al. |
| 2011/0155632 A1* | 6/2011 | Timken ............... C10G 7/00 208/16 |
| 2012/0024750 A1 | 2/2012 | Zhan et al. |
| 2013/0001133 A1* | 1/2013 | Zhan ............... C10G 29/00 208/97 |
| 2013/0062253 A1* | 3/2013 | Timken ............... C10G 35/04 208/64 |
| 2014/0039231 A1* | 2/2014 | Timken ............... B01D 3/009 585/251 |
| 2015/0073188 A1 | 3/2015 | Floudas et al. |
| 2015/0322017 A1 | 11/2015 | Broderick et al. |

OTHER PUBLICATIONS

Kohle., "Chances for innovative processes at the interface between refining and petrochemistry", Report on 10th DGMK International Conference, (2002). v 118, n 12, p. 579-580.

* cited by examiner

CHLORIDE MANAGEMENT IN IONIC LIQUID ALKYLATION PROCESSES

CROSS-REFERENCE TO RELATED APPLICATION

This application claims priority from Provisional Application No. 62/387,127 filed Dec. 23, 2015, the contents of which are hereby incorporated by reference.

BACKGROUND OF THE INVENTION

There are a variety of hydrocarbon conversion processes, and these processes utilize different catalysts.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. ethylbenzene, cumene, dodecylbenzene, etc.).

The alkylation of paraffins with olefins for the production of alkylate for gasoline can use a variety of catalysts. The choice of catalyst depends on the end product a producer desires. Typical alkylation catalysts include concentrated sulfuric acid or hydrofluoric acid. However, sulfuric acid and hydrofluoric acid are hazardous and corrosive, and their use in industrial processes requires a variety of environmental controls.

Solid catalysts are also used for alkylation. However, solid catalysts are very water sensitive and are generally rapidly deactivated by oligomerization of feed olefins to coke, which may block the pores, leading to short active life and the need for expensive regeneration processes.

Acidic ionic liquids can be used as an alternative to the commonly used strong acid catalysts in alkylation processes. Ionic liquids are salts comprised of cations and anions which typically melt below about 100° C. Ionic liquids are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, the ionic liquid can have very different properties.

Ionic liquids provide advantages over other catalysts, including being less corrosive than catalysts like HF, and being non-volatile.

Although ionic liquid catalysts can be very active, alkylation reactions need to be run at low temperatures, typically between −10° C. to 30° C., to maximize the alkylate quality. This requires cooling the reactor and reactor feeds, which adds substantial cost to an alkylation process utilizing ionic liquids in the form of additional equipment and energy. The most common ionic liquid catalysts for alkylation include imidazolium, or pyridinium-based cations coupled with the chloroaluminate anion ($Al_2Cl_7^-$).

In addition, the use of ionic liquids for alkylation requires the use of HCl or an HCl precursor as a co-activator/co-catalyst. The HCl can be introduced into the process in several ways, such as the direct vapor phase injection of HCl to the ionic liquid using anhydrous HCl, or the introduction of a liquid organic chloride. Although the vapor phase method is effective, stringent governmental regulations covering the use of HCl gas may make it impractical. The liquid phase method is less effective because the organic chloride does not readily breakdown to HCl and paraffin in the absence of a catalyst.

Products from the alkylation reactor may contain excess HCl and organic chloride byproducts formed by the reaction of HCl with olefins in the feed, which must be removed from the products to meet specifications and avoid downstream corrosion.

A number of processes have been developed to handle the HCl and organic chlorides in alkylation processes. For example, U.S. Pat. No. 7,538,256 describes an alkylation process using an acidic ionic liquid catalyst and an organic halide promoter. The alkylate formed in the reaction is contacted with a hydrotreating catalyst and hydrogen to reduce the concentration of the organic halide.

U.S. Pat. No. 8,237,004 discusses a process in which the alkylation reactor effluent is sent to a stripper to separate it into a first fraction having an increased amount of hydrogen halide and a bottoms stream having less than 25 ppm hydrogen halide. The first fraction can be recycled to the reactor. The bottoms stream is then sent to a distillation column to be separated into one or more product streams such as an alkylate product stream and isoparaffin streams which can be recycled to the alkylation reactor. The equipment used for recovery is made from materials having poor corrosion resistance to HCl which is said to reduce equipment costs and upstream removal of HCl helps to protect this equipment.

Therefore, there is a need for an integrated system of subprocesses and equipment for more complete handling and control of organic chlorides and HCl in ionic liquid alkylation systems.

SUMMARY OF THE INVENTION

One aspect of the present invention is a process for managing HCl and organic chlorides in an ionic liquid alkylation process. In one embodiment, the process includes reacting an isoparaffin feed stream and an olefin feed stream in an alkylation reaction zone in the presence of an acidic ionic liquid catalyst and an HCl co-catalyst under alkylation conditions to form a reaction mixture comprising alkylate, HCl, organic chlorides, unreacted isoparaffins, and the ionic liquid catalyst. The reaction mixture is separated in an alkylation separation zone into an ionic liquid stream comprising the ionic liquid catalyst, and a hydrocarbon stream comprising the alkylate, the HCl, the organic chlorides, and the unreacted isoparaffins. The hydrocarbon stream is separated in a fractionation zone into at least an isoparaffin-rich recycle stream comprising isoparaffins and HCl, an alkylate stream comprising alkylate and the organic chlorides, and an HCl-rich fractionation overhead stream. The isoparaffin-rich recycle stream is passed to the alkylation reaction zone, wherein the isoparaffin-rich recycle stream comprises at least a part of the isoparaffin feed stream. The alkylate stream is passed to an organic chloride breakdown zone in the presence of hydrogen to convert the organic chlorides to paraffins and HCl and forming an organic chloride breakdown zone effluent stream comprising the alkylate, the paraffins, and HCl. The organic chloride breakdown zone effluent stream is passed to an alkylate stripper column to form an alkylate stripper overhead stream comprising the paraffins and the HCl, and an alkylate product stream. The alkylate stripper overhead stream is passed to the fractionation zone. At least a portion of the HCl-rich fractionation overhead stream is passed to an overhead HCl stripper column forming a paraffin stripper bottoms stream and an HCl rich stripper overhead stream.

DETAILED DESCRIPTION OF THE INVENTION

HCl is present in different concentrations throughout the reaction section of the ionic liquid alkylation process. It is soluble in both the ionic liquid and the hydrocarbon streams. The HCl concentration in the ionic liquid phase is one of the variables in controlling the acidity of the ionic liquid and the selectivity of the alkylate product. Its presence in the spent ionic liquid has an impact on the consumption of regenerant used. If the alkylation unit is integrated with an isomerization unit, which typically has a chlorided alumina catalyst, the isomerized paraffin may also contain soluble HCl. It is desirable for the net product streams from the unit to be HCl and organic chloride free. Adsorbents may be used to remove both HCl and organic chlorides. However, while this may meet the environmental specifications on the products, it is also wasteful because chloride is removed from the process and must ultimately be made up by adding fresh HCl. There is increased consumption of adsorbent, which must be handled as a waste stream, resulting in increased disposal costs. It is therefore preferable to remove the HCl and organic chloride using steps that will keep the chloride within the process unit in a form that can be reused to control the acidity of the ionic liquid.

The present invention involves processes and equipment for handling chloride in an ionic liquid alkylation system. The processes involve not only breaking down the organic chloride to active HCl for ionic liquid activation, but also recovering HCl in the effluent downstream to maintain the HCl requirements while also reducing HCl emissions. In some embodiments, this equipment may be used in conjunction with an isomerization reaction zone which is integrated into the ionic liquid alkylation process to further isomerize n-paraffins to isoparaffins for recycle to the alkylation reaction zone.

The integrated system achieves one or more of: (1) controlling the HCl concentration in the ionic liquid phase in the alkylation reactor to manage the acidity and selectivity of the catalyst; (2) providing HCl and organic chloride free net product streams (alkylate, n-paraffin, light paraffin and fuel gas); (3) minimizing HCl in the spent ionic liquid going to the regeneration process; (4) providing a way to make up for any net HCl losses; (5) allowing for both an HCl-rich isoparaffin-rich recycle stream (e.g., to recycle HCl to the reactor) and an HCl-free isoparaffin stream (e.g., for use in pump seal flushes, as a solvent for the ionic liquid regeneration process, as a regenerant for the olefin feed treaters, and as an extraction solvent for remove of soluble HCl from the spent ionic liquid and regenerant from the regenerated ionic liquid); while (6) minimizing the amount of HCl makeup required and the amount of adsorbent required.

Figure 1:
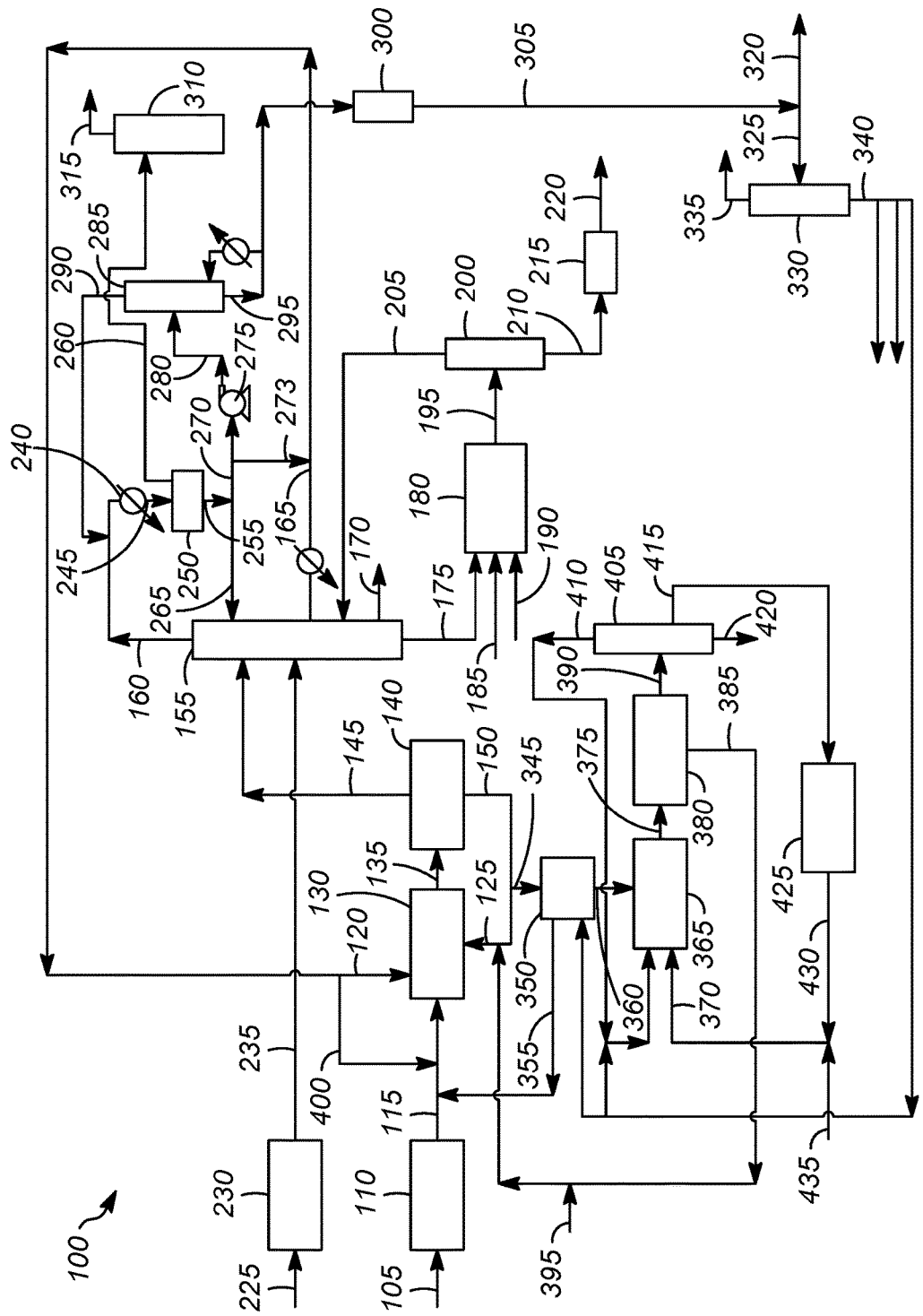
FIG. 1 illustrates one embodiment of an alkylation process according to the present invention.

FIG. 1 illustrates one embodiment of an alkylation process 100 of the present invention.

In some embodiments, the olefin feed 105 is treated in a pretreatment zone 110 to remove water, di-olefins, and sulfur, nitrogen and oxygen compounds. The pretreatment zone 110 can include one or more of a selective hydrogenation unit and one or more adsorbent beds.

The treated olefin stream 115, the isoparaffin feed stream 120 (further described below), and the ionic liquid catalyst stream 125 enter the alkylation reaction zone 130. The ionic liquid catalyst stream 125 catalyzes the alkylation reaction. Both the isoparaffin feed stream 120 and the ionic liquid catalyst stream 125 contain controlled levels of HCl which acts as a co-catalyst to control the acidity of the ionic liquid.

The isoparaffin and olefin can be introduced separately or as a mixture. The molar ratio between the isoparaffin and the olefin is generally in the range of 100:1 to 1:1, or 50:1 to 2:1, or 20:1 to 2:1.

The isoparaffin used in the alkylation process preferably comprises a isoparaffin having from 4 to 10 carbon atoms, or 4 to 8 carbon atoms, or 4 to 5 carbon atoms. The olefin used in the alkylation process preferably has from 2 to 10 carbon atoms, 3 to 8 carbon atoms, or 3 to 5 carbon atoms. One application of the process is to upgrade low value $C_4$ hydrocarbons to higher value alkylate.

To that extent, one specific embodiment is the alkylation of butanes with butylenes to generate $C_8$ compounds. Preferred products include trimethylpentanes (TMP), which have high octane numbers. Other competing $C_8$ isomers are also produced, including dimethylhexanes (DMH), which have lower octane numbers. The quality of the product stream can be measured by the ratio of TMP to DMH, with a high ratio desired.

The ionic liquid can be any acidic ionic liquid. There can be one or more ionic liquids. The ionic liquid comprises an organic cation and an anion. Suitable cations include, but are not limited to, nitrogen-containing cations and phosphorus-containing cations. Suitable organic cations include, but are not limited to:

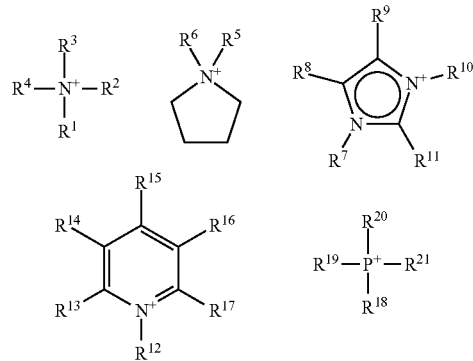

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable.

Lactamium based ionic liquids can also be used including, but not limited to, those described in U.S. Pat. No. 8,709,236, U.S. application Ser. No. 14/271,308, entitled Synthesis of Lactam Based Ionic Liquids, filed May 6, 2014, and U.S. application Ser. No. 14/271,319, entitled Synthesis of N-Derivatized Lactam Based Ionic Liquids, filed May 6, 2014, which are incorporated by reference.

The anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br$). In some embodiments, the metal is aluminum, with the mole fraction of aluminum ranging from $0<Al<0.25$ in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2$, $Cu_2Cl_3^-$, $Cu_3Cl_4^-$, $ZnCl_3^-$, $FeCl_3$, $FeCl_4^-$, $Fe_3Cl_7^-$, $PF_6^-$, and $BF_4^-$.

Most alkylation reactions in ionic liquids are biphasic and take place at the interface in the liquid state due to the low solubility of hydrocarbons in ionic liquids.

The alkylation reaction will proceed simply by contacting the hydrocarbon feed and the ionic liquid catalyst. In some instances, the reaction rate may be too slow to be commercially viable. When mass transfer rate is controlling, the reaction rate can be substantially increased by increasing the mixing intensity of the hydrocarbon feed and the ionic liquid catalyst. After a certain point, increasing the mixing intensity will not provide any additional benefit. Mixing intensity can be controlled using impellers, pumps, static mixers, flow configurations, and baffles, for example. Baffles help to prevent a vortex from forming in the reactor, which would reduce the amount of mixing.

The contacting step may be practiced in laboratory scale experiments through full scale commercial operations. The process may be operated in batch, continuous, or semi-continuous mode. The contacting step can take place in various ways, with both countercurrent and co-current flow processes being suitable.

The reaction time is a function of the degree of mixing, the reaction temperature, and the mass or volume ratio of ionic liquid catalyst to hydrocarbon being reacted. Generally, increasing any of these conditions will increase the reaction rate.

The alkylation reaction is carried out at mild temperatures. In some embodiments, cooling may be needed. If cooling is needed, it can be provided using any known methods.

Typical alkylation reaction conditions include a temperature in the range of about −20° C. to the decomposition temperature of the ionic liquid, or about −20° C. to about 100° C., or about −20° C. to about 80° C., or about 0° C. to about 80° C., or about 20° C. to about 80° C. It is preferred to have an ionic liquid that maintains its liquid state through the operating temperature range.

The pressure is typically in the range of atmospheric (0.1 MPa(g)) to about 8.0 MPa(g), or about 0.3 MPa(g) to about 2.5 MPa(g). The pressure is preferably sufficient to keep the reactants in the liquid phase.

The residence time of the reactants in the reaction zone is in the range of a few seconds to hours, or about 0.5 min to about 60 min, or about 1 min to about 60 min, or about 3 min to about 10 minutes.

Typical alkylation conditions may include a catalyst volume in the reactor of from 1 vol % to 50 vol %, a temperature of from 0° C. to 100° C., a pressure of from 300 kPa to 2500 kPa, an isobutane to olefin molar ratio of from 2 to 20 and a residence time of 1 min to 1 hour.

The effluent 135 from the alkylation reaction zone 130 includes the alkylation reaction products, unreacted isoparaffin, and the ionic liquid catalyst. The effluent 135 is sent to an alkylation separation zone 140 where a hydrocarbon stream 145 containing the alkylation reaction products and unreacted isoparaffin is separated from an ionic liquid stream 150 containing the ionic liquid catalyst. Both the hydrocarbon stream 145 and the ionic liquid stream 150 contain levels of dissolved HCl. The hydrocarbon stream 145 also contains organic chlorides formed by reaction of HCl with the olefin feed. The ionic liquid stream 150 can be recycled to the alkylation reaction zone 130 to form at least a portion of the ionic liquid catalyst stream 125.

The hydrocarbon stream 145 is sent to a fractionation zone 155 where it is separated into a HCl-rich fractionation overhead stream 160, an isoparaffin-rich side-cut recycle stream 165, an n-paraffin-rich side-cut stream 170, and an alkylate bottoms stream 175. By "isoparaffin-rich" we mean the stream contains more than about 50 mol % isoparaffins, or more than about 60 mol %, or more than about 65 mol %, or more than about 70 mol %, or more than about 75 mol %, or about 75 mol % to about 95 mol %. By "n-paraffin-rich" we mean the stream contains more than about 50 mol % n-paraffins, or more than about 60 mol %, or more than about 65 mol %, or more than about 70 mol %, or more than about 75 mol %, or more than about 80 mol %, or about 70 mol % to about 97 mol %.

The isoparaffin-rich recycle stream 165, which contains unreacted isoparaffin from the alkylation reaction zone 130, isoparaffin from the paraffin feed stream 225, and HCl, is recycled to the alkylation reaction zone 130. The isoparaffin-rich recycle stream 165 is at least a portion of the isoparaffin feed stream 120, and is typically the entire stream. The isoparaffin-rich recycle stream 165 allows control of the isoparaffin to olefin ratio in the alkylation reaction and the acidity of the ionic liquid catalyst.

The alkylate bottoms stream 175, which contains alkylate and organic chlorides, is sent to an organic chloride breakdown unit 180. In some embodiments, the alkylate bottoms stream 175 could be sent to an optional ionic liquid guard bed (not shown) to remove ionic liquid before being sent to the organic chloride breakdown unit 180.

In some embodiments, an organic chloride stream 185 is fed to the chloride breakdown reactor as a safe way to introduce makeup HCl to the process, avoiding the issues associated with handling anhydrous HCl. Suitable organic chlorides include, but are not limited to, perchlorides, such as perchloroethylene, and chlorides, such as methyl chloride, methylene chloride, ethyl chloride, dichloroethane, dichloroethylene, trichloroethylene, dichloropropane, dichloropropene, butyl chloride, and carbon tetrachloride.

In the organic chloride breakdown unit 180, the organic chlorides in the alkylate plus any added organic chloride compounds are processed with a stoichiometric amount of hydrogen 190 over a supported noble metal catalyst in a liquid phase reactor to convert the organic chloride into the corresponding paraffin and HCl, for example, t-butyl-chloride to isobutane and HCl. Typical operating conditions for the organic chloride breakdown unit 180 include a temperature of about 100° C. to about 250° C., a pressure of about 1.7 MPa (g) to about 4.1 MPa (g) (about 250 psig to about 600 psig), and a liquid hourly space velocity of about 2.5 hr$^{-1}$ to about 25 hr$^{-1}$. The molar ratio of hydrogen to organic chloride is in the range of about 0.9 to 1.2 of the stoichiometric ratio. The conversion is typically in the range of about 80% to 100%. In some embodiments, the organic chloride breakdown unit 180 is run at incomplete conversion, e.g., about 98% to about 99.5%, by limiting the amount of hydrogen so that the HCL stripper overhead stream 205 of the alkylate stripper column 200 is free of hydrogen.

The effluent 195 from the organic chloride breakdown unit 180 is sent to an alkylate stripper column 200 where it is separated into a HCL stripper overhead stream 205 and an alkylate bottoms stream 210.

The HCL stripper overhead stream 205, which contains paraffins and HCl, is sent to the fractionation zone 155. In some embodiments, the HCL stripper overhead stream 205 is introduced into the fractionation zone 155 to a tray below where the isoparaffin-rich recycle stream 165 is withdrawn. The isoparaffin-rich recycle stream 165 can be heat exchanged with the hydrocarbon stream 145 entering column 155 in a feed-effluent exchanger (not shown).

The alkylate bottoms stream 210 can optionally be sent to a bottoms chloride treater 215, such as an adsorptive treater, to remove any residual organic chloride, forming a chloride and HCl-free alkylate stream 220. The chloride and HCl-free alkylate stream 220 can be sent to product storage or blending. By "chloride and HCl-free" we mean that the alkylate stream contains less than 1 wppm total chloride and HCl.

A paraffin feed stream 225 can be dried in regenerable dryer 230, and the dried paraffin stream 235 can be sent to the fractionation zone 155 to be separated along with the hydrocarbon stream 145. The paraffin feed stream 225 contains n-paraffins and isoparaffins.

The HCl-rich fractionation overhead stream 160 is rich in HCl and may contain light paraffins (e.g., methane, ethane, and/or propane), may be condensed in a condenser 240. Suitable coolants for the condenser include, but are not limited to, water, chilled water, water/glycol mixtures, and the like. With chilled water or a chilled water/glycol mixture, the HCl-rich fractionation overhead stream 160 can be totally condensed so that the HCl and light paraffins (e.g., propane) remain in the liquid phase together with the isobutane. In some embodiments involving the alkylation of butene and isobutane, it is important to lift the isobutane and let it stay in the HCl-rich fractionation overhead stream 160 with appropriate concentration so that the condensed temperature does not go below about 13° C. (about 55° F.), to provide a sensible approach temperature using the chilled water or chilled water/glycol mixture. Even with the presence of isobutane, the total flow of the condensed distillate stream 255 is small.

The condensed overhead stream 245 is sent to an overhead receiver 250 where it is separated into a condensed distillate stream 255 and a vapor stream 260.

The condensed distillate stream 255 is divided into a reflux stream 265 and a condensed distillate stream 270. Reflux stream 265 is returned to the fractionation zone 155 at a level above where the isoparaffin-rich recycle stream is withdrawn.

The condensed distillate stream 270 is pumped in a pump 275, and the liquid stream 280 is sent to an overhead HCl stripper column 285 where liquid stream 280 is separated into an HCl rich stripper overhead stream 290 and a paraffin stripper bottoms stream 295.

In some embodiments, the HCl rich stripper overhead stream 290 is combined with the HCl-rich fractionation overhead stream 160.

In some embodiments, the paraffin stripper bottoms stream 295 is sent to a bottoms chloride treater 300 to form an HCl-free paraffin stream 305.

A portion 273 of the condensed distillate stream 270, which contains isoparaffins (e.g., isobutane) and HCl, is combined with the isoparaffin-rich recycle stream 165 to form the isoparaffin feed stream 120 to the alkylation reaction zone 130.

In some embodiments, the vapor stream 260, which contains noncondensibles and HCl, from the overhead receiver 250 is sent to a scrubber 310, such as a caustic scrubber, where the HCl vapor is removed to provide a clean fuel gas stream 315.

In some embodiments, the HCl-free paraffin stream 305 comprises propane and isobutane, for example. In this case, the HCl-free paraffin stream 305 can be taken off as a product stream 320, or a portion or all of this stream 325 can be depropanized in fractionators 330 to yield a propane stream 335 and an HCl-free isobutane stream 340 that can be used as flush material for pump seals and for drier regeneration. In some embodiments, all or a portion of the HCl-free isobutane stream 340 can be used in the ionic liquid regeneration process. In other embodiments, a similar process can be performed with other paraffins and isoparaffins.

In some embodiments, a portion 345 of the ionic liquid stream 150 can be sent for regeneration. One embodiment of a regeneration process will be described, but other regeneration processes could also be used.

In this embodiment, the portion 345 of the ionic liquid stream 150 is sent to a spent ionic liquid HCl extraction zone 350 where HCl is removed from the ionic liquid forming an HCl-rich isoparaffin stream 355 and an HCl-lean ionic liquid stream 360. In some embodiments, all or a portion of the HCl-free isoparaffin stream 340 may be sent to the spent ionic liquid HCl extraction zone 350. The HCl-rich isoparaffin stream 355 is recycled to the alkylation reaction zone 130.

The HCl lean ionic liquid stream 360 is sent to a regeneration zone 365. A regenerant stream 370, such as a stream of silane or borane compound, is also sent to the regeneration zone 365. In some embodiments, all or a portion of the HCl-free isoparaffin stream 340 is also sent to the regeneration zone 365.

The regenerant reacts with the acid sites of the acidic ionic liquid catalyst. The acid sites that were binding the conjunct polymer are no longer present, which allows the conjunct polymer to be removed.

For example, a silane or borane compound will react with the acid sites in a halometallate ionic liquid to form a silyl or boryl halide. Regeneration processes utilizing silane and borane compounds are described in U.S. application Ser. Nos. 14/269,943 and 14/269,978, each of which is incorporated herein by references.

The deactivated acidic catalyst and the regenerant are contacted for a period of time sufficient to allow the conjunct polymer to react with the regenerant. This will typically take in the range of about 5 sec to about 1 hr, or about 1 min to about 45 min, or about 1 min to about 30 min, or about 1 min to about 15 min.

The contacting typically takes place at a temperature in the range of from about −20° C. to the decomposition temperature of the ionic liquid. A typical temperature range is about 20° C. to about 80° C. In some embodiments, the contacting takes place at room temperature. In other embodiments, the contacting takes place at about 40° C. to about 80° C., or about 70° C.

The pressure is typically high enough to keep the solvent and regenerant in the liquid phase at the operating temperature.

In some embodiments, the reaction is conducted under an inert gas so that hydrolysis of the regenerant and/or the ionic liquid does not occur. Suitable inert gases include, but are not limited to, nitrogen, helium, neon, argon, krypton, and xenon.

In one embodiment, the regeneration process is a solvent extraction process. In the solvent extraction method, a solvent and a regenerant are added to the ionic liquid containing conjunct polymer. The solvent and the regenerant can be pre-mixed and added together, or they can be added separately, either at the same time or sequentially. Solvent is not always necessary, but it will maximize recovery, removal, and separation of the conjunct polymer. In some embodiments, the volume ratio of the solvent to the deactivated acidic ionic liquid is in a range of about 0.25:1 to about 10:1.

In some embodiments, the molar ratio of the regenerant to the conjunct polymer is in a range of about 0.5:1 to about 5:1, or about 2:1 to about 3:1. In some embodiments, the regenerant can be present in excess of the amount needed for reaction with the conjunct polymer, and the excess regenerant can act as a solvent. In these cases, the molar ratio of the regenerant to the conjunct polymer is more than 5:1, e.g., in the range of 10:1 to about 1000:1.

The contacting can take place in any suitable process, such as solvent extraction, or contacting in one or more mixer/settlers.

The reaction will proceed simply by contacting the regenerant with the acidic ionic liquid catalyst. However, the mixture can be stirred to increase the contact between the regenerant and the acidic ionic liquid catalyst.

The contacting step may be practiced in laboratory scale experiments through full scale commercial operations. The process may be operated in batch, continuous, or semi-continuous mode. The contacting step can take place in various ways, with both countercurrent and co-current flow processes being suitable. The order of addition of the reactants is not critical. For example, the reactants can be added individually, or some reactants may be combined or mixed before being combined or mixed with other reactants.

After contacting the acidic ionic liquid catalyst and the regenerant, two phases result, a catalyst phase containing the acidic ionic liquid catalyst and an organic phase containing the conjunct polymer, the reacted regenerant compound, and solvent, if present.

The effluent 375 from the regeneration zone 365 is sent to a regeneration separation zone 380 where it is separated into a regenerated ionic liquid stream 385 and a hydrocarbon stream 390.

In some embodiments, the regeneration separation zone 380 is a gravity settler where the phases separate due to the density difference between the two phases. In other embodiments, other separation processes may be used. Suitable separation zones include, but are not limited to, one or more of gravity settlers, coalescers, centrifugation units, and decanting units.

The regenerated ionic liquid stream 385 is recycled to the alkylation reaction zone 130. Make-up ionic liquid catalyst 395 can be added as needed to the regenerated ionic liquid stream 385, the ionic liquid stream 150, and/or the ionic liquid catalyst stream 125.

The hydrocarbon stream 390, which contains the conjunct polymer, unreacted regenerant, solvent, and the reacted regenerant compound, can be further processed to recover and recycle the solvent. The hydrocarbon stream 390 can be sent to a solvent column 405 where it is separated into solvent recycle stream 410, which contains the solvent and any unreacted regenerant, a reacted regenerant stream 415, and a bottoms stream 420 containing the conjunct polymer.

The reacted regenerant stream 415 can be treated in a regenerant recovery zone 425 to form a recovered regenerant stream 430. Recovered regenerant stream 430 can be combined with make-up regenerant stream 435 to form the regenerant stream 370.

In some embodiments, the reacted regenerant can be chemically reduced to recover the regenerant. For example, silyl or boryl halides can be reduced to silane or borane compounds. One method of regeneration is reaction with one or more compounds containing hydrogen, such as one or more metal hydrides. The silyl or boryl compound is converted back to the silane or borane compound and a metal salt byproduct. Suitable metal hydrides include, but are not limited to, $LiH$, $NaH$, $CaH_2$, $NaAlH_4$, $LiAlH_4$, $KH$, $NaBH_4$, diisobutylaluminum hydride, and the like.

Other methods for regenerating ionic liquids could be used. For example, U.S. Pat. Nos. 7,651,970; 7,825,055; 7,956,002; 7,732,363, each of which is incorporated herein by reference, describe contacting ionic liquid containing conjunct polymer with a reducing metal (e.g., Al), an inert hydrocarbon (e.g., hexane), and hydrogen and heating to about 100° C. to transfer the conjunct polymer to the hydrocarbon phase, allowing for the conjunct polymer to be removed from the ionic liquid phase. Another method involves contacting ionic liquid containing conjunct polymer with a reducing metal (e.g., Al) in the presence of an inert hydrocarbon (e.g. hexane) and heating to about 100° C. to transfer the conjunct polymer to the hydrocarbon phase, allowing for the conjunct polymer to be removed from the ionic liquid phase. See e.g., U.S. Pat. No. 7,674,739 B2; which is incorporated herein by reference. Still another method of regenerating the ionic liquid involves contacting the ionic liquid containing the conjunct polymer with a reducing metal (e.g., Al), HCl, and an inert hydrocarbon (e.g. hexane), and heating to about 100° C. to transfer the conjunct polymer to the hydrocarbon phase. See e.g., U.S. Pat. No. 7,727,925, which is incorporated herein by reference. The ionic liquid can be regenerated by adding a homogeneous metal hydrogenation catalyst (e.g., $(PPh_3)_3RhCl$) to ionic liquid containing conjunct polymer and an inert hydrocarbon (e.g. hexane), and introducing hydrogen. The conjunct polymer is reduced and transferred to the hydrocarbon layer. See e.g., U.S. Pat. No. 7,678,727, which is incorporated herein by reference. Another method for regenerating the ionic liquid involves adding HCl, isobutane, and an inert hydrocarbon to the ionic liquid containing the conjunct polymer and heating to about 100° C. The conjunct polymer reacts to form an uncharged complex, which transfers to the hydrocarbon phase. See e.g., U.S. Pat. No. 7,674,740, which is incorporated herein by reference. The ionic liquid could also be regenerated by adding a supported metal hydrogenation catalyst (e.g. Pd/C) to the ionic liquid containing the conjunct polymer and an inert hydrocarbon (e.g. hexane). Hydrogen is introduced and the conjunct polymer is reduced and transferred to the hydrocarbon layer. See e.g., U.S. Pat. No. 7,691,771, which is incorporated herein by reference. Still another method involves adding a suitable substrate (e.g. pyridine) to the ionic liquid containing the conjunct polymer. After a period of time, an inert hydrocarbon is added to wash away the liberated conjunct polymer. The ionic liquid precursor [butylpyridinium][Cl] is added to the ionic liquid (e.g. [butylpyridinium][Al$_2$Cl$_7$]) containing the conjunct polymer followed by an inert hydrocarbon. After mixing, the hydrocarbon layer is separated, resulting in a regenerated ionic liquid. See, e.g., U.S. Pat. No. 7,737,067, which is incorporated herein by reference. Another method involves adding ionic liquid containing conjunct polymer to a suitable substrate (e.g. pyridine) and an electrochemical cell containing two aluminum electrodes and an inert hydrocarbon. A voltage is applied, and the current measured to determine the extent of reduction. After a given time, the inert hydrocarbon is separated, resulting in a regenerated ionic liquid. See, e.g., U.S. Pat. No. 8,524,623, which is incorporated herein by reference. Ionic liquids can also be regenerated by contacting with Brønsted acids, (U.S. application Ser. No. 14/229, 329), or C$_1$ to C$_{10}$ Paraffins (U.S. application Ser. No. 14/229,403), each of which is incorporated herein by reference.

Figure 2:
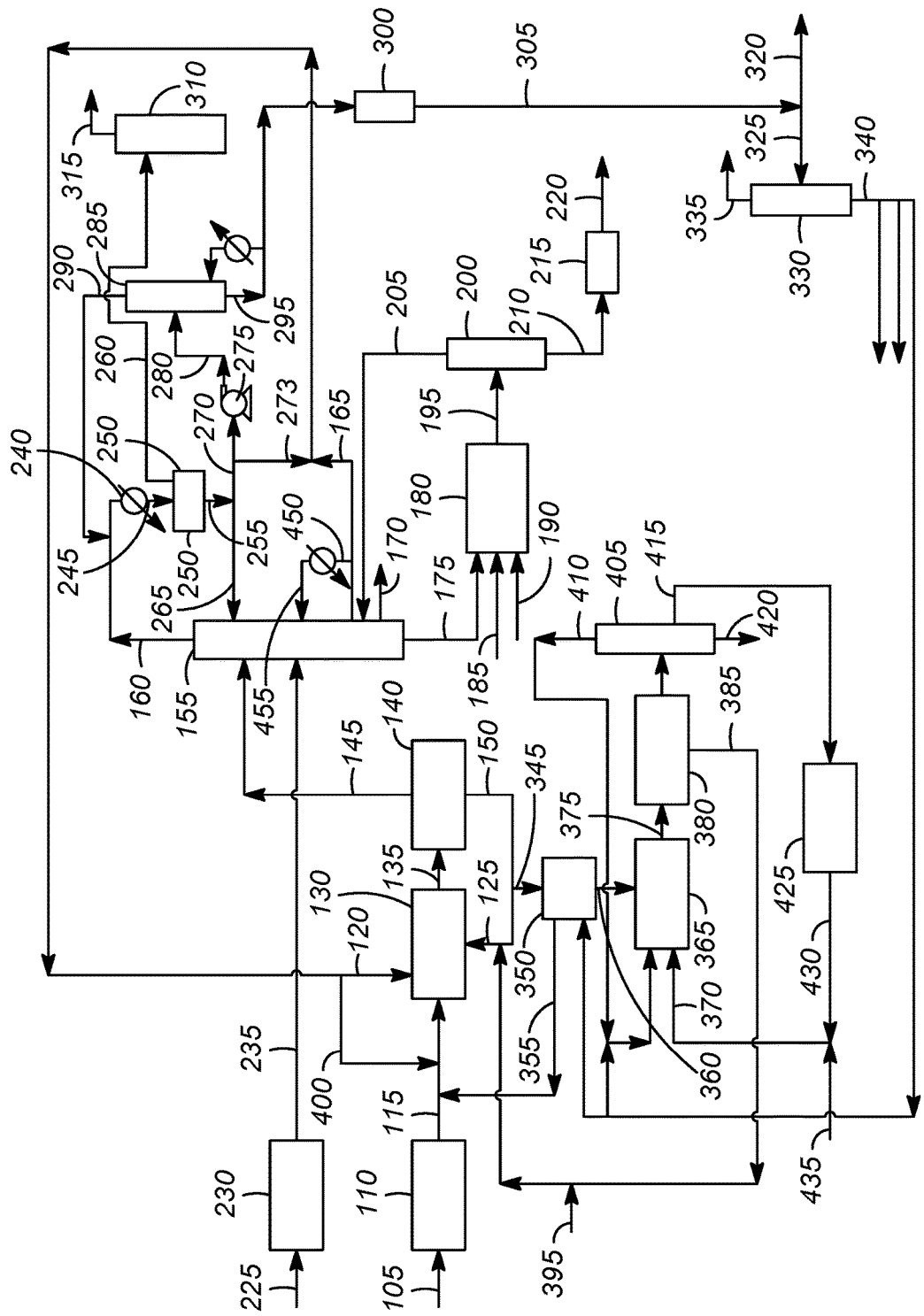
FIG. 2 illustrates another embodiment of an alkylation process according to the present invention.

FIG. 2 illustrates another embodiment of the process. It is generally similar to FIG. 1. The difference is a reduction of the cooling load (chilled water) at the condenser 240 by using a pump-around of a portion 450 the isoparaffin-rich recycle stream 165. The portion 450 is cooled with cooling water or heat exchanged with hydrocarbon stream 145 entering column 155 in a feed-effluent exchanger (not shown), and the cooled stream 455 is returned to the fractionation zone 155 at a level above where the HCl stripper overhead stream 205 enters the fractionation zone 155. Thus, the use of chilled water is minimized, reducing the operating cost.

Figure 3:
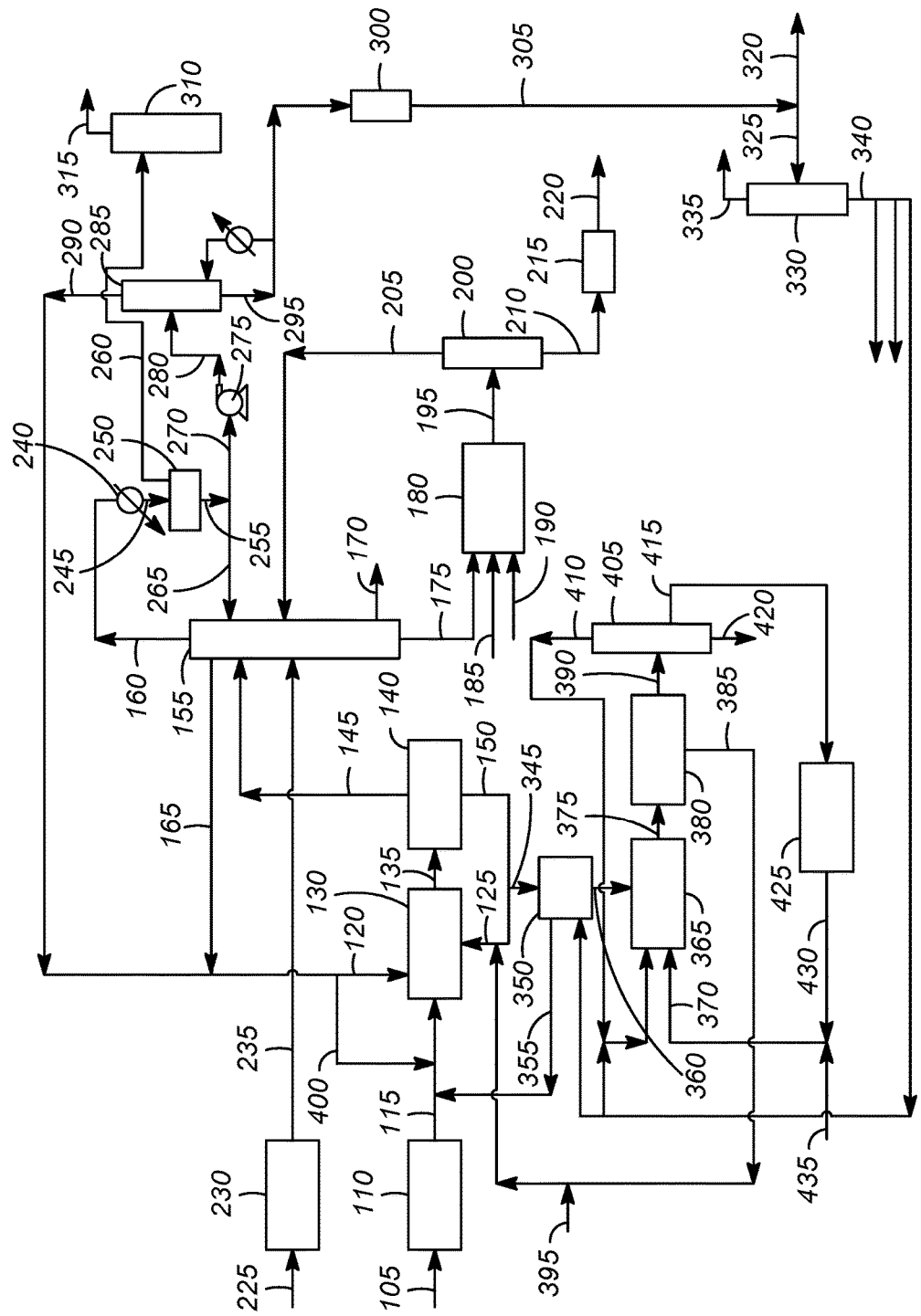
FIG. 3 illustrates yet another embodiment of an alkylation process according to the present invention.

FIG. 3 shows another embodiment of the process. It is generally similar to FIG. 1, except that in this case, the condensed distillate stream 270 is not combined with the isoparaffin-rich recycle stream 165. Instead, the HCl rich stripper overhead stream 290 is combined with the isoparaffin-rich recycle stream 165.

Figure 4:
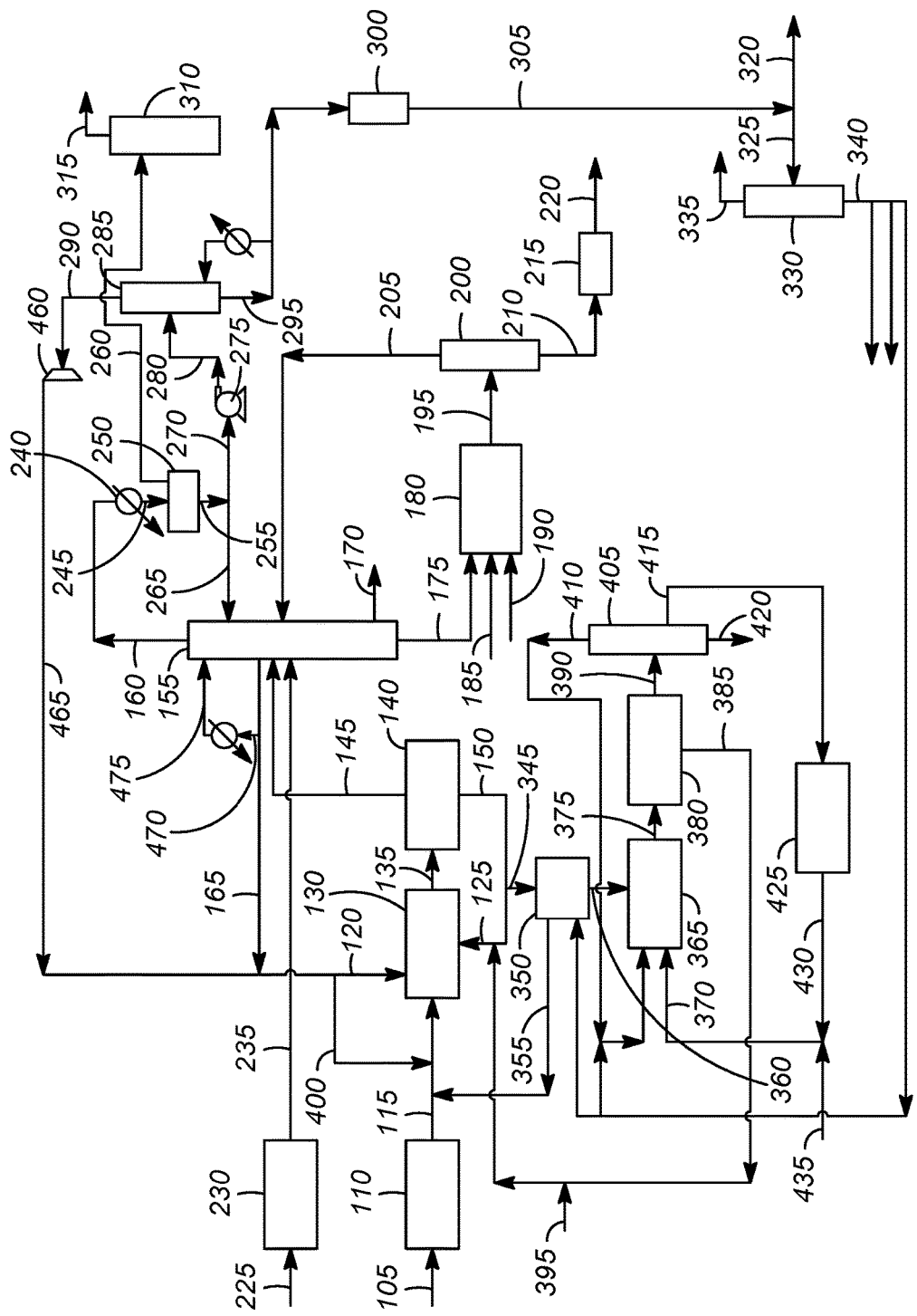
FIG. 4 illustrates still another embodiment of an alkylation process according to the present invention.

Another embodiment is shown in FIG. 4. It is generally similar to FIG. 3. However, in this embodiment, the HCl rich stripper overhead stream 290 is compressed in a compressor 460. The compressed HCl rich stripper overhead stream 465 is combined with the isoparaffin-rich recycle stream 165. In addition, the cooling load on the condenser 240 is reduced by using a pump-around of a portion 470 of the isoparaffin-rich recycle stream 165. The portion 470 is cooled with cooling water or heat exchanged with hydrocarbon stream 145 entering column 155 in a feed-effluent exchanger (not shown), and the cooled stream 475 is returned to the fractionation zone 155 at a level above where the HCL stripper overhead stream 205 enters the fractionation zone 155.

Figure 5:
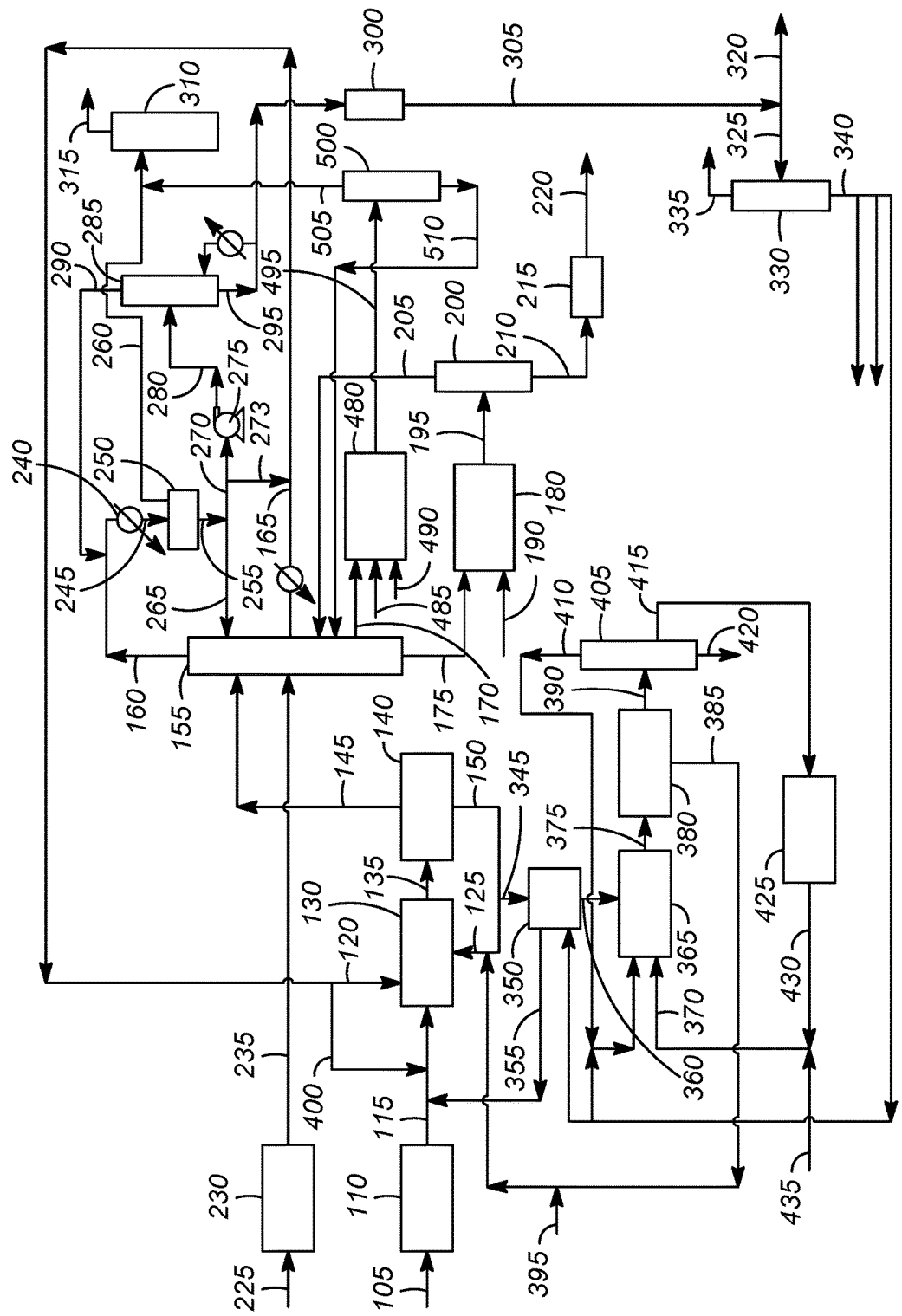
FIG. 5 illustrates another embodiment of an alkylation process according to the present invention.

FIG. 5 is generally similar to FIG. 1. In this embodiment, the n-paraffin-rich stream 170 is sent to an isomerization zone 480 along with an organic chloride stream 485 and a hydrogen stream 490 where at least a portion of the n-paraffins are converted to isoparaffins. Typical isomerization conditions include a temperature of about 140° C. to about 210° C. (about 284° F. to about 410° F.), a pressure of about 2.8 MPa (g) to about 4.1 MPa (g) (about 400 psig to about 600 psig), and a liquid hourly space velocity of about 2 hr$^{-1}$ to about 8 hr$^{-1}$. In recycle gas type units, the molar ratio of hydrogen to hydrocarbon is about 0.15 to about 0.40, and in hydrogen once through units, the molar ratio of hydrogen to hydrocarbon is about −0.01 to 0.5 measured at the reactor outlet.

The organic chloride stream 485 can replace the organic chloride stream 185 which is introduced into the organic chloride breakdown unit 180 as shown in FIG. 1. Alternatively, it can be in addition to the organic chloride stream 185.

The isomerization effluent stream 495, which contains isomerized paraffins and HCl, is sent to a stabilizer column 500 where it is separated into a stabilizer overhead vapor stream 505 and a stabilizer bottoms stream 510.

The stabilizer overhead vapor stream 505 is sent to the scrubber 310.

The stabilizer bottoms stream 510 is introduced into the fractionation zone 155 at a level above where the n-paraffin-rich stream 170 was withdrawn and below the level where the isoparaffin-rich recycle stream 165 is withdrawn.

Figure 6:
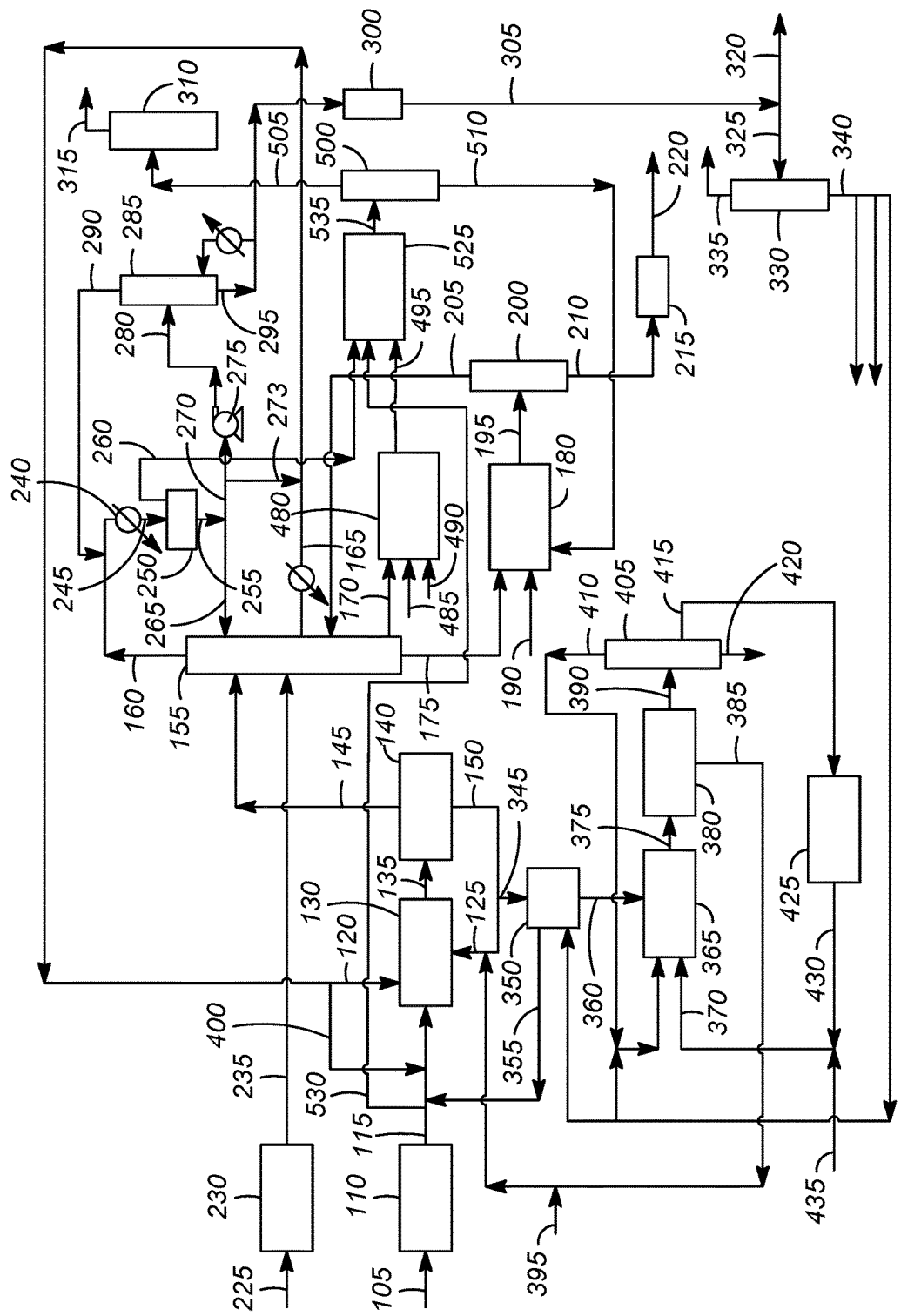
FIG. 6 illustrates yet another embodiment of an alkylation process according to the present invention.

FIG. 6 is generally similar to FIG. 5. In this embodiment, the isomerization effluent stream 495 is sent to HCl/olefin reactor 525. The purpose of this reactor is to convert excess HCl to organic chlorides to retain HCl in the system and minimize the amount of organic chloride injection makeup and caustic treating required on the offgas streams going to flare. The vapor stream 260 from the overhead receiver 250 is sent to the HCl/olefin reactor 525 and reacted with a stoichiometric amount of olefin feed provided by slip stream 530. The olefin and HCl easily react over a variety of catalysts at moderate conditions, for example an alumina bed at about 20-45° C. (about 68-113° F.), to form an organic chloride of the same carbon number as the olefin. The treated isomerized effluent stream 535 comprising isomerized paraffins and organic chlorides is sent to the stabilizer column 500. The stabilizer overhead vapor stream 505 is sent to the scrubber 310. The stabilizer bottoms stream 510 is sent to the organic chloride breakdown unit 180.

Figure 7:
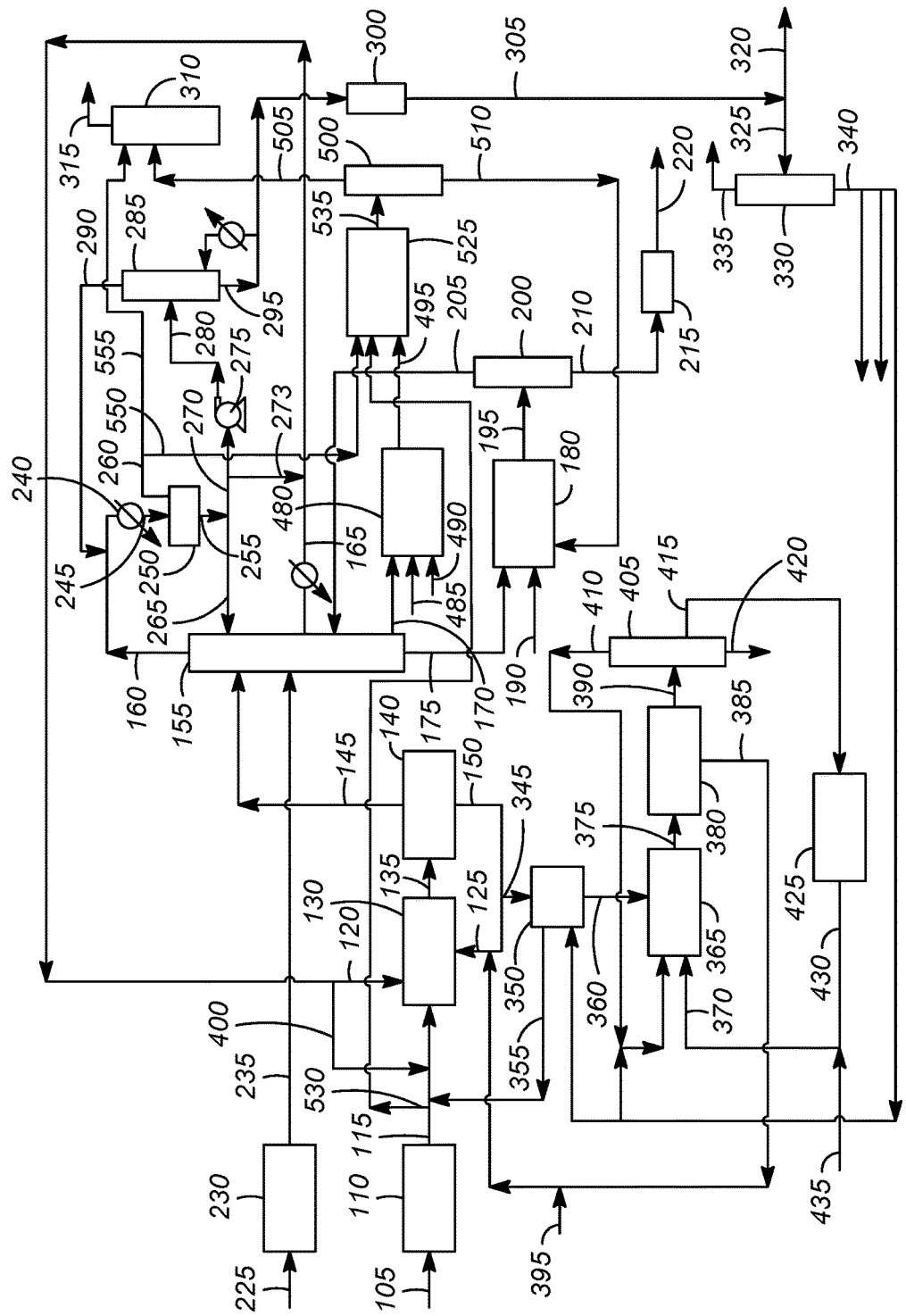
FIG. 7 illustrates still another embodiment of an alkylation process according to the present invention.

FIG. 7 is generally similar to FIG. 6. However in this embodiment, a portion 550 of the vapor stream 260 from the overhead receiver 250 is sent to the HCl/olefin reactor 525. Another portion 555 is sent to the scrubber 310.

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for managing HCl and organic chlorides in an ionic liquid alkylation process comprising reacting an isoparaffin feed stream and an olefin feed stream in an alkylation reaction zone in the presence of an acidic ionic liquid catalyst and an HCl co-catalyst under alkylation conditions to form a reaction mixture comprising alkylate, HCl, organic chlorides, unreacted isoparaffins, and the ionic liquid catalyst; separating the reaction mixture in an alkylation separation zone into an ionic liquid stream comprising the ionic liquid catalyst, and a hydrocarbon stream comprising the alkylate, the HCl, the organic chlorides, and the unreacted isoparaffins; separating the hydrocarbon stream in a fractionation zone into at least an isoparaffin-rich recycle stream comprising isoparaffins and HCl, an alkylate stream comprising alkylate and the organic chlorides, and an HCl-rich fractionation overhead stream; passing the isoparaffin-rich recycle stream to the alkylation reaction zone, wherein the isoparaffin-rich recycle stream comprises at least a part of the isoparaffin feed stream; passing the alkylate stream to an organic chloride breakdown zone in the presence of hydrogen to convert the organic chlorides to paraffins and HCl and forming an organic chloride breakdown zone effluent stream comprising the alkylate, the paraffins, and HCl; passing the organic chloride breakdown zone effluent stream to an alkylate stripper column to form to form an alkylate stripper overhead stream comprising the paraffins and the HCl, and an alkylate product stream; passing the alkylate stripper overhead stream to the fractionation zone; and passing at least a portion of the HCl-rich fractionation overhead stream to an overhead HCl stripper column and forming a paraffin stripper bottoms stream and an HCl rich stripper overhead stream. An embodiment of the invention is one, any or all of prior embodiments in this paragraph up through the first embodiment in this paragraph further comprising introducing a paraffin feed stream comprising isoparaffins and n-paraffins into the fractionation zone; and wherein separating the hydrocarbon stream into at least the isoparaffin-rich recycle stream, the alkylate stream, and the HCl-rich fractionation overhead stream comprises separating the hydrocarbon stream and the paraffin feed stream into at least the isoparaffin-rich recycle stream, the alkylate stream, the HCl-rich fractionation overhead stream, and an n-paraffin rich stream. An embodiment of the invention is one, any or all of prior embodiments in this paragraph up through the first embodiment in this paragraph further comprising introducing an organic chloride stream into the organic chloride breakdown zone. An embodiment of the invention is one, any or all of prior embodiments in this paragraph up through the first embodiment in this paragraph further comprising combining a portion of the HCl-rich fractionation overhead stream with the isoparaffin-rich recycle stream; and optionally combining the HCl rich stripper overhead stream with the HCl-rich fractionation overhead stream. An embodiment of the invention is one, any or all of prior embodiments in this paragraph up through the first embodiment in this paragraph further comprising combining the HCl rich stripper overhead stream with the isoparaffin-rich recycle stream. An embodiment of the invention is one, any or all of prior embodiments in this paragraph up through the first embodiment in this paragraph further comprising compressing at least a portion of the HCl-rich stripper overhead stream before combining the HCl rich stripper overhead stream with the isoparaffin-rich recycle stream. An embodiment of the invention is one, any or all of prior embodiments in this paragraph up through the first embodiment in this paragraph wherein separating the hydrocarbon stream into at least the isoparaffin-rich recycle stream, the alkylate stream, and the HCl-rich fractionation overhead stream comprises separating the hydrocarbon phase into at least the isoparaffin-rich recycle stream, the alkylate stream, the HCl-rich fractionation overhead stream, and an n-paraffin rich stream, and further comprising passing the n-paraffin rich stream, an organic chloride stream, and hydrogen to an isomerization zone to form an isomerized effluent stream comprising isomerized paraffins and HCl; separating the isomerized effluent stream in a stabilizer column into a stabilizer overhead vapor stream and a stabilizer bottoms stream comprising the isomerized paraffins; introducing the stabilizer bottoms stream into the fractionation zone at a level above where the n-paraffin rich stream is withdrawn to feed the isomerization zone and below a level where the isoparaffin-rich recycle stream is withdrawn from the fractionation zone. An embodiment of the invention is one, any or all of prior embodiments in this paragraph up through the first embodiment in this paragraph further comprising passing the stabilizer overhead vapor stream into a scrubber. An embodiment of the invention is one, any or all of prior embodiments in this paragraph up through the first embodiment in this paragraph wherein separating the hydrocarbon stream into at least the isoparaffin-rich recycle stream, the alkylate stream, and the HCl-rich fractionation overhead stream comprises separating the hydrocarbon phase into at least the isoparaffin-rich recycle stream, the alkylate stream, the HCl-rich fractionation overhead stream, and an n-paraffin rich stream, and further comprising passing the n-paraffin rich stream, an organic chloride stream, and hydrogen to an isomerization zone to form an isomerized effluent stream comprising isomerized paraffins and HCl; passing the isomerized effluent, and an olefin stream to an HCl/olefin reactor in the presence of a catalyst to form a treated isomerized effluent stream comprising isomerized paraffins and organic chlorides; separating the isomerized effluent stream in a stabilizer column into a stabilizer overhead vapor stream and a stabilizer bottoms stream comprising the isomerized paraffins; introducing the stabilizer bottoms stream into the organic breakdown unit; and optionally passing the stabilizer overhead vapor stream into a scrubber. An embodiment of the invention is one, any or all of prior embodiments in this paragraph up through the first embodiment in this paragraph further comprising condensing the HCl-rich fractionation overhead stream; separating the condensed overhead stream into a liquid portion and a vapor portion; and passing at least a portion of the vapor portion to the HCl/olefin reactor. An embodiment of the invention is one, any or all of prior embodiments in this paragraph up through the first embodiment in this paragraph further comprising condensing the HCl-rich fractionation overhead stream; separating the condensed overhead stream into a liquid portion and a vapor portion; and passing a portion of the vapor portion to a scrubber. An embodiment of the invention is one, any or all of prior embodiments in this paragraph up through the first embodiment in this paragraph further comprising recycling the ionic liquid stream to the alkylation reaction zone. An embodiment of the invention is one, any or all of prior embodiments in this paragraph up through the first embodiment in this paragraph further comprising regenerating at least a portion of the ionic liquid stream in a regeneration zone; and recycling at least a portion of the regenerated ionic liquid stream to the alkylation reaction zone. An embodiment of the invention is one, any or all of prior embodiments in this paragraph up through the first embodiment in this paragraph further comprising passing the alkylate product stream to an alkylate chloride treater to provide a chloride and HCl-free alkylate product stream. An embodiment of the invention is one, any or all of prior embodiments in this paragraph up through the first embodiment in this paragraph further comprising passing the paraffin bottoms stream to a bottoms chloride treater to provide an HCl-free paraffin stream. An embodiment of the invention is one, any or all of prior embodiments in this paragraph up through the first embodiment in this paragraph further comprising introducing at least a portion of the HCl-free paraffin stream to an HCl removal zone; removing HCl from at least a portion of the ionic liquid stream in the HCl removal zone to form an HCl rich stream and an HCl reduced ionic liquid stream; regenerating the HCl reduced ionic liquid stream in a regeneration zone; and recycling the regenerated ionic liquid stream to the alkylation reaction zone. An embodiment of the invention is one, any or all of prior embodiments in this paragraph up through the first embodiment in this paragraph wherein at least about 80% of the organic chlorides are converted to HCl in the organic chloride breakdown zone.

A second embodiment of the invention is a process for managing HCl and organic chlorides in an ionic liquid alkylation process comprising reacting an isoparaffin feed stream and an olefin feed stream in an alkylation reaction zone in the presence of an acidic ionic liquid catalyst and an HCl co-catalyst under alkylation conditions to form a reaction mixture comprising alkylate, HCl, organic chlorides, unreacted isoparaffins, and the ionic liquid catalyst; separating the reaction mixture in an alkylation separation zone into an ionic liquid stream comprising the ionic liquid catalyst, and a hydrocarbon stream comprising the alkylate, the HCl, the organic chlorides, and the unreacted isoparaffins; introducing a paraffin feed stream comprising isoparaffins and n-paraffins into a fractionation zone; separating the hydrocarbon stream and the paraffin feed stream in the fractionation zone into at least an isoparaffin-rich recycle stream comprising isoparaffins and HCl, an n-paraffin-rich stream, an alkylate stream comprising alkylate and the organic chlorides, and an HCl-rich fractionation overhead stream comprising HCl and $C_{3-}$ gases, passing the isoparaffin-rich recycle stream to the alkylation reaction zone, wherein the isoparaffin-rich recycle stream comprises at least a part of the isoparaffin feed stream; introducing an organic chloride stream into an organic chloride breakdown zone; passing the alkylate stream to the organic chloride breakdown zone in the presence of hydrogen to convert the organic chlorides to paraffins and HCl and forming an organic chloride breakdown zone effluent stream comprising the alkylate, the paraffins, and HCl, and wherein at least about 80% of the organic chloride is converted HCl in the organic chloride breakdown zone; passing the organic chloride breakdown zone effluent stream to an alkylate stripper column to form an alkylate stripper overhead stream comprising the paraffins and the HCl, and an alkylate product stream; passing the alkylate stripper overhead stream to the fractionation zone at a level above where the isoparaffin-rich recycle stream is withdrawn from the fractionation zone; passing at least a portion of the HCl-rich fractionation overhead stream to an overhead HCl stripper column and forming a paraffin stripper bottoms stream and an HCl rich stripper overhead stream; passing the alkylate product stream to an alkylate chloride treater to provide a chloride and HCl-free alkylate product stream; and passing the paraffin stripper bottoms stream to a bottoms chloride treater to provide an HCl-free paraffin stream. An embodiment of the invention is one, any or all of prior embodiments in this paragraph up through the second embodiment in this paragraph further comprising passing the n-paraffin-rich stream, a second organic chloride stream, and hydrogen to an isomerization zone to form an isomerized effluent stream comprising isomerized paraffins and HCl; separating the isomerized effluent stream in a stabilizer column into a stabilizer overhead vapor stream and a bottoms stream comprising the isomerized paraffins; introducing the bottoms stream into the fractionation zone at a level above where the n-paraffin-rich stream is removed from the fractionation zone and below a level where the isoparaffin stream is removed from the fractionation zone. An embodiment of the invention is one, any or all of prior embodiments in this paragraph up through the second embodiment in this paragraph further comprising regenerating at least a portion of the ionic liquid stream in a regeneration zone; recycling at least a portion of the regenerated ionic liquid stream to the alkylation reaction zone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for managing HCl and organic chlorides in an ionic liquid alkylation process comprising:
    reacting an isoparaffin feed stream and an olefin feed stream in an alkylation reaction zone in the presence of an acidic ionic liquid catalyst and an HCl co-catalyst under alkylation conditions to form a reaction mixture comprising alkylate, HCl, organic chlorides, unreacted isoparaffins, and the ionic liquid catalyst;
    separating the reaction mixture in an alkylation separation zone into an ionic liquid stream comprising the ionic liquid catalyst, and a hydrocarbon stream comprising the alkylate, the HCl, the organic chlorides, and the unreacted isoparaffins;
    separating the hydrocarbon stream in a single fractionation column into at least an isoparaffin-rich recycle stream comprising isoparaffins and HCl, an alkylate stream comprising alkylate and the organic chlorides, and an HCl-rich fractionation overhead stream comprising HCl, isobutane, and $C_{3-}$ gases;
    passing the isoparaffin-rich recycle stream to the alkylation reaction zone, wherein the isoparaffin-rich recycle stream comprises at least a part of the isoparaffin feed stream;
    passing the alkylate stream to an organic chloride breakdown zone in the presence of hydrogen to convert the organic chlorides to paraffins and HCl and forming an organic chloride breakdown zone effluent stream comprising the alkylate, the paraffins, and HCl;
    passing the organic chloride breakdown zone effluent stream to an alkylate stripper column to form an alkylate stripper overhead stream comprising the paraffins and the HCl, and an alkylate product stream;
    passing the alkylate stripper overhead stream to the single fractionation column; and
    passing at least a portion of the HCl-rich fractionation overhead stream to an overhead HCl stripper column and forming a paraffin stripper bottoms stream comprising isobutane and $C_{3-}$ hydrocarbons and an HCl rich stripper overhead stream comprising noncondensables and HCl.

2. The process of claim 1 further comprising:
    introducing a paraffin feed stream comprising isoparaffins and n-paraffins into the fractionation zone; and wherein separating the hydrocarbon stream into at least the isoparaffin-rich recycle stream, the alkylate stream, and the HCl-rich fractionation overhead stream comprises separating the hydrocarbon stream and the paraffin feed stream into at least the isoparaffin-rich recycle stream, the alkylate stream, the HCl-rich fractionation overhead stream, and an n-paraffin rich stream.

3. The process of claim 1 further comprising introducing an organic chloride stream into the organic chloride breakdown zone.

4. The process of claim 1 further comprising:
combining a portion of the HCl-rich fractionation overhead stream with the isoparaffin-rich recycle stream; and
optionally combining the HCl rich stripper overhead stream with the HCl-rich fractionation overhead stream.

5. The process of claim 1 further comprising:
combining the HCl rich stripper overhead stream; and
combining at least a portion of the condensed HCl rich stripper overhead stream with the isoparaffin-rich recycle stream.

6. The process of claim 5 further comprising compressing at least a portion of the HCl-rich stripper overhead stream before combining the HCl rich stripper overhead stream with the isoparaffin-rich recycle stream.

7. The process of claim 1 wherein separating the hydrocarbon stream into at least the isoparaffin-rich recycle stream, the alkylate stream, and the HCl-rich fractionation overhead stream comprises separating the hydrocarbon phase into at least the isoparaffin-rich recycle stream, the alkylate stream, the HCl-rich fractionation overhead stream, and an n-paraffin rich stream, and further comprising:
passing the n-paraffin rich stream, an organic chloride stream, and hydrogen to an isomerization zone to form an isomerized effluent stream comprising isomerized paraffins and HCl;
separating the isomerized effluent stream in a stabilizer column into a stabilizer overhead vapor stream and a stabilizer bottoms stream comprising the isomerized paraffins;
introducing the stabilizer bottoms stream into the fractionation zone at a level above where the n-paraffin rich stream is withdrawn to feed the isomerization zone and below a level where the isoparaffin-rich recycle stream is withdrawn from the fractionation zone.

8. The process of claim 7 further comprising: passing the stabilizer overhead vapor stream into a scrubber.

9. The process of claim 1 wherein separating the hydrocarbon stream into at least the isoparaffin-rich recycle stream, the alkylate stream, and the HCl-rich fractionation overhead stream comprises separating the hydrocarbon phase into at least the isoparaffin-rich recycle stream, the alkylate stream, the HCl-rich fractionation overhead stream, and an n-paraffin rich stream, and further comprising:
passing the n-paraffin rich stream, an organic chloride stream, and hydrogen to an isomerization zone to form an isomerized effluent stream comprising isomerized paraffins and HCl;
passing the isomerized effluent, and an olefin stream to an HCl/olefin reactor in the presence of a catalyst to form a treated isomerized effluent stream comprising isomerized paraffins and organic chlorides;
separating the isomerized effluent stream in a stabilizer column into a stabilizer overhead vapor stream and a stabilizer bottoms stream comprising the isomerized paraffins;
introducing the stabilizer bottoms stream into the organic chloride breakdown zone; and
optionally passing the stabilizer overhead vapor stream into a scrubber.

10. The process of claim 9 further comprising:
condensing the HCl-rich fractionation overhead stream;
separating the condensed overhead stream into a liquid portion and a vapor portion; and
passing at least a portion of the vapor portion to the HCl/olefin reactor.

11. The process of claim 1 further comprising:
condensing the HCl-rich fractionation overhead stream;
separating the condensed overhead stream into a liquid portion and a vapor portion; and
passing a portion of the vapor portion to a scrubber.

12. The process of claim 1 further comprising recycling the ionic liquid stream to the alkylation reaction zone.

13. The process of claim 1 further comprising:
regenerating at least a portion of the ionic liquid stream in a regeneration zone; and
recycling at least a portion of the regenerated ionic liquid stream to the alkylation reaction zone.

14. The process of claim 1 further comprising passing the alkylate product stream to an alkylate chloride treater to provide a chloride and HCl-free alkylate product stream.

15. The process of claim 1 further comprising passing the paraffin stripper bottoms stream to a bottoms chloride treater to provide an HCl-free paraffin stream.

16. The process of claim 15 further comprising:
introducing at least a portion of the HCl-free paraffin stream to an HCl removal zone, wherein the HCl-free paraffin stream is used to remove the HCl from the ionic liquid;
removing HCl from at least a portion of the ionic liquid stream in the HCl removal zone to form an HCl rich stream and an HCl reduced ionic liquid stream;
recycling the HCl rich stream to the alkylation reaction zone;
regenerating the HCl reduced ionic liquid stream in a regeneration zone; and
recycling the regenerated ionic liquid stream to the alkylation reaction zone.

17. The process of claim 1 wherein at least about 80% of the organic chlorides are converted to HCl in the organic chloride breakdown zone.

18. A process for managing HCl and organic chlorides in an ionic liquid alkylation process comprising:
reacting an isoparaffin feed stream and an olefin feed stream in an alkylation reaction zone in the presence of an acidic ionic liquid catalyst and an HCl co-catalyst under alkylation conditions to form a reaction mixture comprising alkylate, HCl, organic chlorides, unreacted isoparaffins, and the ionic liquid catalyst;
separating the reaction mixture in an alkylation separation zone into an ionic liquid stream comprising the ionic liquid catalyst, and a hydrocarbon stream comprising the alkylate, the HCl, the organic chlorides, and the unreacted isoparaffins;
introducing a paraffin feed stream comprising isoparaffins and n-paraffins into a single fractionation column;
separating the hydrocarbon stream and the paraffin feed stream in the single fractionation column into at least an isoparaffin-rich recycle stream comprising isoparaffins and HCl, an n-paraffin-rich stream, an alkylate stream comprising alkylate and the organic chlorides, and an HCl-rich fractionation overhead stream comprising HCl, isobutane, and $C_{3-}$ gases;

passing the isoparaffin-rich recycle stream to the alkylation reaction zone, wherein the isoparaffin-rich recycle stream comprises at least a part of the isoparaffin feed stream;

introducing an organic chloride stream into an organic chloride breakdown zone;

passing the alkylate stream to the organic chloride breakdown zone in the presence of hydrogen to convert the organic chlorides to paraffins and HCl and forming an organic chloride breakdown zone effluent stream comprising the alkylate, the paraffins, and HCl, and wherein at least about 80% of the organic chloride is converted HCl in the organic chloride breakdown zone;

passing the organic chloride breakdown zone effluent stream to an alkylate stripper column to form an alkylate stripper overhead stream comprising the paraffins and the HCl, and an alkylate product stream;

passing the alkylate stripper overhead stream to the single fractionation column at a level below where the isoparaffin-rich recycle stream is withdrawn from the fractionation zone;

passing at least a portion of the HCl-rich fractionation overhead stream to an overhead HCl stripper column and forming a paraffin stripper bottoms stream comprising isobutane and $C_{3-}$ hydrocarbon and an HCl rich stripper overhead stream comprising noncondensables and HCl;

passing the alkylate product stream to an alkylate chloride treater to provide a chloride and HCl-free alkylate product stream; and passing the paraffin stripper bottoms stream to a bottoms chloride treater to provide an HCl-free paraffin stream.

19. The process of claim 18 further comprising:

passing the n-paraffin-rich stream, a second organic chloride stream, and hydrogen to an isomerization zone to form an isomerized effluent stream comprising isomerized paraffins and HCl;

separating the isomerized effluent stream in a stabilizer column into a stabilizer overhead vapor stream and a bottoms stream comprising the isomerized paraffins;

introducing the bottoms stream into the fractionation zone at a level above where the n-paraffin-rich stream is removed from the fractionation zone and below a level where the isoparaffin stream is removed from the fractionation zone.

20. The process of claim 18 further comprising regenerating at least a portion of the ionic liquid stream in a regeneration zone and recycling at least a portion of the regenerated ionic liquid stream to the alkylation reaction zone.

* * * * *